(12) United States Patent
Sage

(10) Patent No.: US 12,134,558 B2
(45) Date of Patent: Nov. 5, 2024

(54) PROCESS FOR PREPARING HYDRAZINE HYDRATE WITH PYRAZOLINE RECYCLING

(71) Applicant: Arkema France, Colombes (FR)

(72) Inventor: Jean-Marc Sage, Pierre-Benite (FR)

(73) Assignee: Arkema France, Colombes (FR)

( * ) Notice: Subject to any disclaimer, the term of this patent is extended or adjusted under 35 U.S.C. 154(b) by 535 days.

(21) Appl. No.: 17/611,443

(22) PCT Filed: May 12, 2020

(86) PCT No.: PCT/FR2020/050789
§ 371 (c)(1),
(2) Date: Nov. 15, 2021

(87) PCT Pub. No.: WO2020/229774
PCT Pub. Date: Nov. 19, 2020

(65) Prior Publication Data
US 2022/0227627 A1    Jul. 21, 2022

(30) Foreign Application Priority Data
May 16, 2019  (FR) .................................. 1905110

(51) Int. Cl.
C07C 45/42    (2006.01)
C01B 21/16    (2006.01)

(52) U.S. Cl.
CPC .............. *C01B 21/16* (2013.01); *C07C 45/42* (2013.01)

(58) Field of Classification Search
None
See application file for complete search history.

(56) References Cited

U.S. PATENT DOCUMENTS

| | | |
|---|---|---|
| 3,948,902 A | 4/1976 | Schirmann et al. |
| 3,972,876 A | 8/1976 | Schirmann et al. |
| 3,972,878 A | 8/1976 | Schirmann et al. |
| 4,093,656 A | 6/1978 | Schirmann et al. |
| 4,657,751 A | 8/1987 | Alicot et al. |
| 4,724,133 A | 2/1988 | Schirmann et al. |
| 4,725,421 A | 2/1988 | Schirmann et al. |
| 4,963,232 A | 10/1990 | Kuriyama et al. |
| 5,239,119 A | 8/1993 | Schirmann et al. |
| 5,252,309 A | 10/1993 | Krempf et al. |
| 6,517,798 B1 | 2/2003 | Schirmann et al. |

(Continued)

FOREIGN PATENT DOCUMENTS

| | | |
|---|---|---|
| DE | 3873185 T2 | 3/1993 |
| EP | 0070155 A1 | 1/1983 |

(Continued)

OTHER PUBLICATIONS

International Search Report and Written Opinion for International Application No. PCT/FR2020/050789, dated Sep. 29, 2020, 7 pages.

*Primary Examiner* — Sudhakar Katakam
*Assistant Examiner* — Jennifer C Sawyer
(74) *Attorney, Agent, or Firm* — Buchanan Ingersoll & Rooney PC

(57) ABSTRACT

The present invention relates to an improved process for preparing hydrazine hydrate from the azine of methyl ethyl ketone obtained from methyl ethyl ketone by oxidizing ammonia with hydrogen peroxide in the presence of an activator, characterized in that it comprises a step of recycling the pyrazoline-class heterocycles purge.

10 Claims, 1 Drawing Sheet

(56) References Cited

U.S. PATENT DOCUMENTS

| | | |
|---|---|---|
| 6,605,265 B1 | 8/2003 | Schirmann et al. |
| 6,759,023 B1 | 7/2004 | Brenguer et al. |

FOREIGN PATENT DOCUMENTS

| | | |
|---|---|---|
| EP | 0153216 A1 | 8/1985 |
| EP | 0179699 A1 | 4/1986 |
| EP | 0399866 A1 | 11/1990 |
| EP | 0487160 A1 | 5/1992 |
| EP | 0518728 A1 | 12/1992 |
| FR | 1315348 A | 1/1963 |
| GB | 1164460 | 9/1969 |
| GB | 1211547 | 11/1970 |
| WO | 9958445 A1 | 11/1999 |
| WO | 0037357 A1 | 6/2000 |
| WO | 2018065997 A1 | 4/2018 |

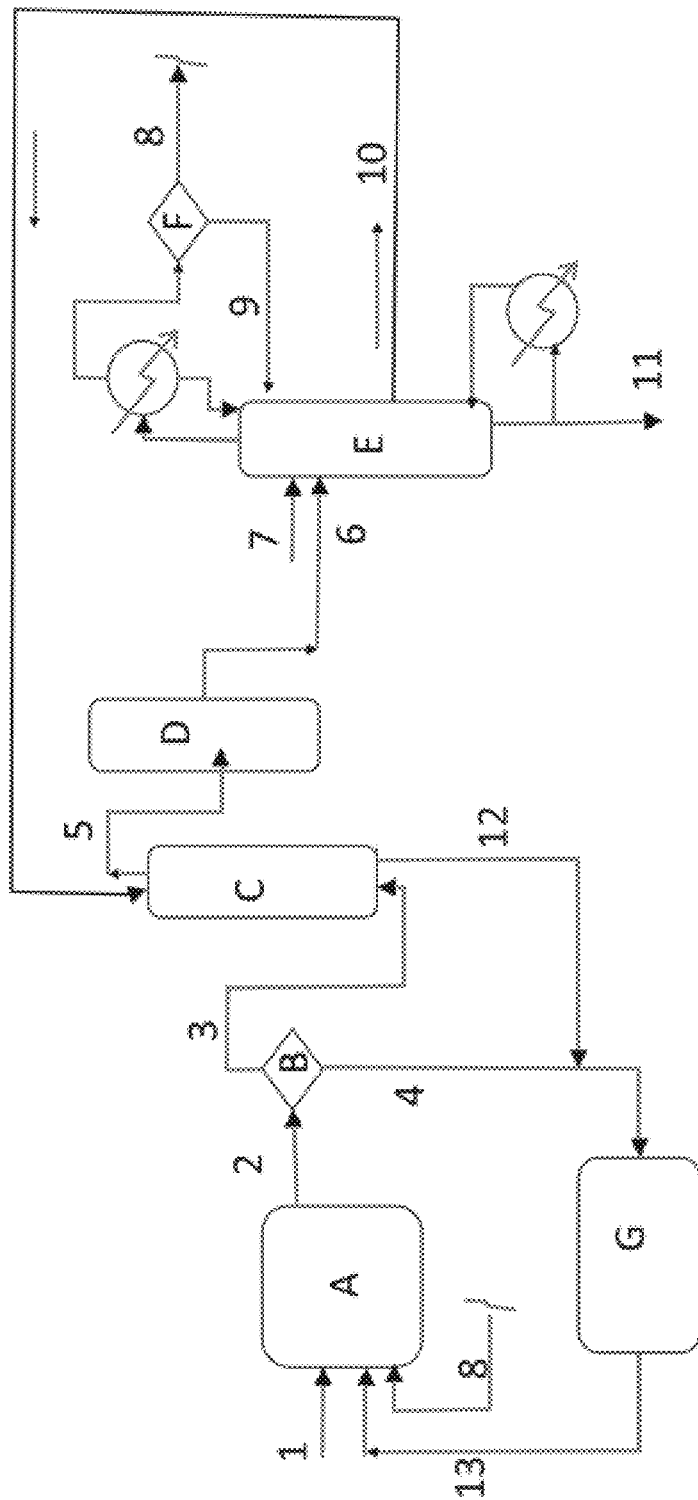

PROCESS FOR PREPARING HYDRAZINE HYDRATE WITH PYRAZOLINE RECYCLING

CROSS-REFERENCE TO RELATED APPLICATIONS

This application is the national phase of International Application No. PCT/FR2020/050789, filed 12 May 2020, which claims priority to French Application No. FR 1905110, filed 16 May 2019. the disclosure of each of these applications being incorporated herein by reference in its entirety for all purposes.

FIELD OF THE INVENTION

The present invention relates to a process for preparing hydrazine hydrate. The present invention relates more specifically to an improved process for preparing hydrazine hydrate from the azine of methyl ethyl ketone obtained in the presence of methyl ethyl ketone by oxidizing ammonia with hydrogen peroxide and an activator.

BACKGROUND OF THE INVENTION

Hydrazine is employed in a variety of different applications, primarily in the deoxygenation of boiler waters (of nuclear power stations, for example), and is used for preparing pharmaceutical and agrochemical derivatives.

There is therefore an industrial need for the preparation of hydrazine hydrate.

Hydrazine hydrate is produced industrially by the Raschig or Bayer processes or with hydrogen peroxide.

The Raschig process sees ammonia oxidized with a hypochlorite to give a dilute solution of hydrazine hydrate, which must then be concentrated by distillation. This process, being relatively unselective, relatively unproductive and highly polluting, is virtually no longer employed.

The Bayer process is a variant of the Raschig process and involves shifting a chemical equilibrium by using acetone to trap the resulting hydrazine in the form of an azine with the formula below: $(CH_3)_2C{=}N{-}N{=}C{-}(CH_3)_2$.

The azine is subsequently isolated and then hydrolyzed to hydrazine hydrate. Yields are improved, but there is no improvement in environmental emissions.

The process with hydrogen peroxide involves oxidizing a mixture of ammonia and a ketone with hydrogen peroxide in the presence of a means of activating the hydrogen peroxide to make the azine directly, which then need only be hydrolyzed to hydrazine hydrate. The yields are high and the process is nonpolluting. Numerous patents describe this hydrogen peroxide process, examples being U.S. Pat. Nos. 3,972,878, 3,972,876, 3,948,902 and 4,093,656.

Hydrolysis of an azine to hydrazine hydrate is described in patents U.S. Pat. No. 4,724,133 Schirmann et al., U.S. Pat. No. 4,725,421 Schirmann et al., and GB 1 164 460. This hydrolysis takes place in a distillation column which is fed with water and the azine. The ketone is recovered at the top and a concentrated hydrazine hydrate solution at the bottom.

These processes are also described in Ullmann's Encyclopedia of Industrial Chemistry (1989), vol. A 13, pages 182-183 and the references included.

In the hydrogen peroxide processes, ammonia is oxidized with hydrogen peroxide in the presence of a ketone and a means of activating the hydrogen peroxide according to the overall reaction below, making an azine:

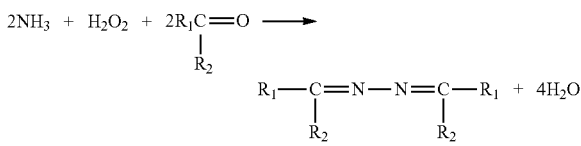

The means of activating—or activator—may be a nitrile, an amide, a carboxylic acid or else a selenium, antimony or arsenic derivative. The azine is then hydrolyzed to hydrazine, and the ketone is regenerated according to the reaction below:

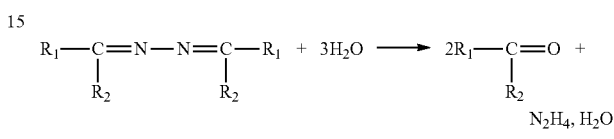

This hydrolysis is actually performed in two stages, with formation of an intermediate hydrazone:

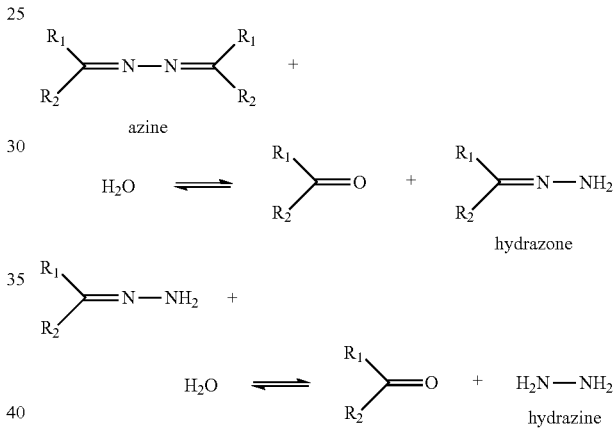

Whether the azine is produced by a hydrogen peroxide process or another process, methyl ethyl ketone is used advantageously on account of its low solubility in an aqueous medium.

The reason is that in the hydrogen peroxide process, the azine of methyl ethyl ketone is relatively insoluble in the reaction mixture, which is necessarily aqueous owing to the use of commercial aqueous solutions of hydrogen peroxide with a concentration of between 30% and 70% by weight. Thus, this azine is easy to recover and can be isolated simply by decanting. It is highly stable particularly in an alkaline environment, viz. in the ammoniacal reaction mixture. In the current processes, this azine is subsequently purified and then hydrolyzed in a reactive distillation column eventually to afford methyl ethyl ketone at the top for recycling, and particularly an aqueous solution of hydrazine hydrate at the bottom, which is required to contain as few carbonaceous products as impurities as possible and to be colorless.

In these hydrogen peroxide processes employing methyl ethyl ketone (also called MEK), however, small amounts are formed of byproducts, and especially of heterocycles from the class of pyrazoline. These byproducts are more particularly 3,4,5-trimethyl-5-ethylpyrazoline and 3,5-diethyl-5-methylpyrazoline, with the following formulas:

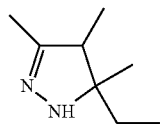 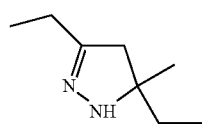

3,4,5-trimethyl-5-ethyl pyrazoline   3,5-diethyl-5-methyl pyrazoline

These compounds are isomers of the azine of methyl ethyl ketone. They form principally in the hydrolysis column, and are responsible for coloring the hydrazine yellow, or even brown or red. At the bottom of the column, therefore, there may be a hydrazine hydrate solution obtained which, rather than being colorless, is colored—sometimes highly so— depending on the amount of heterocycles from the class of pyrazoline obtained.

These byproducts may accumulate on the trays of the hydrolysis column, causing the coloration problems described above and operating problems beyond a certain concentration. The amount of pyrazoline-class heterocycles is preferably not more than 5% by weight, more preferably between 1% and 3% by weight, relative to the total weight of the liquid phase on the trays of the column or in the parts of the hydrolysis column at which said amount is at its maximum. These levels are sufficient to avoid coloration of the hydrazine hydrate produced.

There is therefore a need for an industrial process for preparing hydrazine hydrate that is improved in respect of the treatment of byproducts such as the pyrazoline-class heterocycles, and more particularly 3,4,5-trimethyl-5-ethylpyrazoline and 3,5-diethyl-5-methylpyrazoline.

Document WO 99/58445 describes purging the pyrazoline-class heterocycles discontinuously during the step in which the azine is hydrolyzed to hydrazine hydrate. It is noted that these compounds form in the hydrolysis column.

This document, though, gives no indication as to any treatment of this purge.

There is therefore a need for an improved process for preparing hydrazine hydrate wherein the byproducts are treated in a manner more economical and more environmentally friendly.

SUMMARY OF THE INVENTION

It has surprisingly been found that when the purge of pyrazoline-class heterocycles is recycled upstream of the hydrolysis step, these byproducts are dissolved in the azine on entry to the distillation step (e) and are removed during this distillation step. The distillation step enables removal, surprisingly, of the pyrazoline-class heterocycles. Furthermore, the hydrazine precursors (azine and hydrazone) which may be contained in this purge are recovered in the azine stream and return to the hydrolysis column.

Recycling in accordance with the invention enables the concentration of pyrazoline-class heterocycles in the hydrolysis column to be stabilized, at a concentration low enough to give a colorless hydrazine hydrate solution at the bottom of the hydrolysis column and to do so stably when the hydrolysis is operated continuously.

Recycling the pyrazoline-class heterocycles purge in accordance with the invention hence has many advantages. Discharge of an effluent containing the azine and the hydrazone is avoided, these being intermediate products leading to hydrazine, while the byproducts are removed from the process, without adding operations or additional cost to the process.

If the effluent containing said heterocycles were to be discharged, an additional treatment would need to be implemented, such as incineration or oxidizing treatment, for example, before it was emitted into the environment.

The process according to the invention also retains the azine and hydrazone compounds which may be contained in the purge, as the hydrazone and the azine lead via hydrolysis to hydrazine hydrate.

The present invention hence relates to a process for preparing hydrazine hydrate, comprising the following steps:

(a) reacting ammonia, hydrogen peroxide and methyl ethyl ketone in the presence of a solution comprising at least one activator to form an azine;

(b) treating the reaction mixture from step (a) to isolate:
the aqueous phase comprising the activator(s); and
the organic phase comprising the resulting azine and optionally the unreacted methyl ethyl ketone;

(c) optionally recycling the aqueous phase to step (a) after optional treatment;

(d) washing the organic phase, preferably in countercurrent;

(e) distilling the washed organic phase to recover the azine;

(f) hydrolyzing the azine to give hydrazine hydrate and regenerate methyl ethyl ketone, with pyrazoline-class heterocycles being purged;

(g) optionally recycling the methyl ethyl ketone obtained in step (f) to step (a), (h) recycling the pyrazoline-class heterocycles purge obtained in step (f) to one at least of steps (a), (b), (c), (d) or (g).

The pyrazoline-class heterocycles purge comprises, obviously, said heterocycles, but may also comprise azine, hydrazone and water. Said purge is especially in aqueous form.

The set of steps of the process are preferably carried out continuously.

DETAILED DESCRIPTION OF THE INVENTION

The term "pyrazoline-class heterocycles" refers especially to a pyrazoline ring substituted on at least one of its carbon atoms, and more particularly to a pyrazoline ring of formula (I) below:

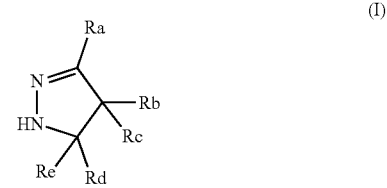

(I)

in which Ra, Rb, Rc, Rd and Re may be selected independently of one another from H and the $(C_1-C_{20})$alkyls, with at least one of the radicals Ra, Rb, Rc, Rd and Re being a $(C_1-C_{20})$alkyl.

The term "$(C_1-C_{20})$alkyl" denotes saturated aliphatic hydrocarbons which may be linear or branched and which comprise from 1 to 20 carbon atoms. Preferably the alkyls comprise from 1 to 4 carbon atoms, or even from 1 to 2 carbon atoms. Mention may be made, for example, of methyl and ethyl. The term "branched" is understood to mean that an alkyl group is substituted along the main alkyl chain.

"Azine" refers in particular to the azine of methyl ethyl ketone, which is also called mekazine.

(a): Formation of the Azine of Methyl Ethyl Ketone

In step (a) ammonia, hydrogen peroxide and methyl ethyl ketone are reacted in the presence of a solution comprising at least one activator to form an azine, viz. the azine of methyl ethyl ketone.

The ammonia may be anhydrous or in aqueous solution.

The hydrogen peroxide may be used in its common commercial form, as for example in aqueous solution at between 30% and 90% by weight of $H_2O_2$. It is possible advantageously to add one or more customary stabilizers for peroxide solutions, as for example phosphoric, pyrophosphoric, citric, nitrilotriacetic or ethylenediaminetetraacetic acid or the ammonium or alkali metal salts of these acids. The amount to be used is advantageously between 10 and 1000 ppm and preferably between 50 and 250 ppm of the entirety of the reactants and the solution comprising at least one activator at the entry of the reactor.

An "activator" refers to a compound allowing the hydrogen peroxide to be activated, i.e., a compound enabling the azine to be produced from ammonia, hydrogen peroxide and methyl ethyl ketone.

This activator may be selected from organic or inorganic oxyacids, ammonium salts thereof and derivatives thereof: anhydrides, esters, amides, nitriles, acyl peroxides, or mixtures thereof. Use is made advantageously of amides, ammonium salts and nitriles.

Mention may be made, by way of example, of:
(i) amides of carboxylic acids of formula $R_5COOH$ in which $R_5$ is hydrogen, a linear alkyl radical having from 1 to 20 carbon atoms, or a branched or cyclic alkyl radical having from 3 to 12 carbon atoms, or an unsubstituted or substituted phenyl radical,
(ii) amides of polycarboxylic acids of formula $R_6(COOH)_n$ in which $R_6$ represents an alkylene radical having from 1 to 10 carbon atoms and n is an integer not less than 2; $R_6$ may be a single bond, in which case n is 2.

The radicals $R_5$ and $R_6$ may be substituted by halogens or by OH, $NO_2$ or methoxy groups. Mention may also be made of the amides of organic acids of arsenic. Organic acids of arsenic are, for example, methylarsonic acid, phenylarsonic acid and cacodylic acid.

The preferred amides are formamide, acetamide, monochloroacetamide and propionamide, and more preferably acetamide.

Ammonium salts advantageously used are the salts of hydracids, of inorganic oxyacids, of arylsulfonic acids, of acids of formula $R_5COOH$ or $R_6(COOH)_n$, where $R_5$, $R_6$ and n are as defined above, and of organic acids of arsenic.

Preferred ammonium salts are formate, acetate, monochloroacetate, propionate, phenylarsonate and cacodylate.

Nitriles that may advantageously be mentioned are the products of formula $R_7(CN)_n$, where n may range from 1 to 5 depending on the valence of $R_7$, $R_7$ is a cyclic or noncyclic alkyl having from 1 to 12 carbon atoms or a benzyl or a pyridinyl group. $R_7$ may be substituted by groups which are not oxidized in the reactor of step (a), as for example halogens, carboxyl groups, carboxylic esters, nitro, amine, hydroxyl or sulfonic acid.

Preferred nitriles are acetonitrile and propionitrile.

The solution comprising at least one activator is formed by dissolving one or more products selected from organic or inorganic oxyacids, ammonium salts thereof and derivatives thereof: anhydrides, esters, amides, nitriles, acyl peroxides, or mixtures thereof as defined above. It is advantageous to use the above nitriles, ammonium salts or amides. Particular preference is given to using a single activator, namely acetamide.

This solution may be aqueous or based on an alcohol or on a mixture of an alcohol and water. Alcohols used advantageously are saturated aliphatic alcohols having from 1 to 6 carbon atoms and preferably 1 to 2 carbon atoms.

Also used advantageously are diols, and more particularly diols having from 2 to 5 carbon atoms. Examples include glycol, propylene glycol, 1,3-propanediol, 1,3- and 1,4-butanediol and 1,5-pentanediol.

In one embodiment said solution is an alcoholic solution of an organic acid of arsenic and is described in patent EP 0 070 155.

In another embodiment said solution is an aqueous solution of an amide of a weak acid and the ammonium salt corresponding to this acid, as described in patent EP 0 487 160.

These weak-acid amides are derivatives of the corresponding carboxylic acids having a dissociation constant of less than $3 \times 10^{-3}$, in other words of acids having a pK of more than 3 in aqueous solution at 25° C.

For polycarboxylic acids, the acids in question are those for which the first ionization constant is less than $3 \times 10^{-3}$.

Examples include carboxylic acids of formula $R_8COOH$ in which $R_8$ is a linear alkyl radical having from 1 to 20 carbon atoms, or a branched or cyclic alkyl radical having from 3 to 12 carbon atoms, or an unsubstituted or substituted phenyl radical, and polycarboxylic acids of formula $R_9(COOH)_n$ in which $R_9$ represents an alkylene radical having from 1 to 10 carbon atoms and n is a number not less than 2; $R_9$ may be a single bond, in which case n is 2. The radicals $R_8$ and $R_9$ may be substituted by halogens or by OH, $NO_2$ or methoxy groups. Preference is given to using acetamide, propionamide, n-butyramide or isobutyramide.

The corresponding ammonium salt of acetamide is ammonium acetate.

It would not be outside the scope of the invention to form the ammonium salt in situ, in other words to use the corresponding carboxylic acid which, by reaction with ammonia, gives the ammonium salt.

The proportions of the amide and of the corresponding ammonium salt may vary within wide limits. It is common to use from 1 to 25 parts of the ammonium salt to 5 parts of amide and preferably 2 to 10.

The reactants may be used in stoichiometric amounts. It is, however, possible to use 0.2 to 5 moles and preferably 1.5 to 4 moles of methyl ethyl ketone, and from 0.1 to 10 moles and preferably from 1.5 to 4 moles of ammonia, per mole of hydrogen peroxide. The amount of solution comprising at least one activator may be between 0.1 and 2 kg per mole of hydrogen peroxide. This amount is dependent on its quality, i.e., on its catalytic strength or its activity which enables conversion of the reactants to azine. The above-stipulated proportions of the reactants enable total conversion of the hydrogen peroxide and production of azine corresponding to more than 50% of the hydrogen peroxide employed, and possibly reaching 90%.

The hydrogen peroxide, the ammonia and the methyl ethyl ketone may be contacted in any way with the solution comprising at least one activator.

It is possible to employ a homogeneous medium or a medium which ensures solubilization of the reactants at least to an extent allowing the azine to be obtained. The reaction may proceed within a very wide temperature range, between 0° C. and 100° C. for example, and is operated advantageously between 30° C. and 70° C. Although operable at any pressure, it is simpler to be at atmospheric pressure, although an increase to up to approximately 10 bar is possible if necessary in order preferably to maintain the reaction of step (a) in liquid phase.

The reactants may be introduced simultaneously or separately and in any order into the solution comprising at least one activator.

Any sorts of reactors may be used, with or without agitation, or even simple tanks, which may be arranged in parallel or in series, cocurrentwise or countercurrentwise, or any combination of these possibilities.

Following the reaction of step (a), therefore, a reaction mixture is obtained comprising the resulting azine, optionally the unreacted methyl ethyl ketone, optionally the activator(s), and optionally other byproducts or impurities.

Step (b): Phase Separation

The aqueous phase comprising the activator(s) is separated from the organic phase comprising the resulting azine and optionally the unreacted methyl ethyl ketone by conventional means such as liquid-liquid extraction, distillation, decanting or any combination of these possibilities. Decanting is preferably used.

The organic phase obtained may comprise the azine and unreacted methyl ethyl ketone, activator(s), and optionally impurities.

Step (c): Recycling of the Aqueous Phase

In step (c) the aqueous phase may be treated before recycling to step (a), conventionally for example by thermal regeneration with optional subsequent concentration.

Steps (a), (b) and (c) are described for example in patents EP 399 866 and EP 518 728.

Step (d): Washing of the Organic Phase

The step of washing the organic phase obtained in step (b) is a step which may be carried out by techniques known to the person skilled in the art, as indicated for example in document WO 2018/065997 (p. 13, "Organic layer processing section", second paragraph). In particular, the washing step allows recovery of the activator(s), acetamide for example, possibly still present in the organic phase.

Washing may be performed in a countercurrent washing column.

Washing is preferably performed countercurrentwise by the pyrazoline-class heterocycles purge performed in hydrolysis step (f), optionally after addition of water. Washing may be performed by all or part of said purge. More preferably still, the purge is sufficient to perform washing, with no water added, thus allowing especially a saving to be made of an additional water intake in the process.

For example, the pyrazoline-class heterocycles purge as defined above is added at the column top and the organic phase to be washed is added at the column bottom. The activator(s) possibly still present in the organic phase thus pass(es) into the aqueous washing phase (viz. the pyrazoline-class heterocycles purge).

In one embodiment, after passage through the washing column, the resultant aqueous phase either is recycled to step (a) with the aqueous phase recovered in step (b), or else may be returned directly to the hydrolysis column.

Step (e): Distillation of the Organic Phase

The step of distilling the washed organic phase is a step which may be carried out by techniques known to the person skilled in the art, as indicated for example in document WO 2018/065997 (p. 13, "Organic layer processing section"), especially in a distillation column.

The distillation step is used to separate the azine from the pyrazoline-class heterocycles as defined above and from other heavy impurities, having a high boiling point. These byproducts are recovered at the column bottom, for example.

The distillation step is also used to separate the azine formed in step (a) from the unreacted methyl ethyl ketone, which may be recovered at the column top. The methyl ethyl ketone thus recovered may be recycled to the azine synthesis step (a).

Hence at the end of the washing and distillation steps a purified organic phase is obtained, comprising the azine.

Step (f): Hydrolysis of the Azine, Regeneration of the MEK and Purge of the Pyrazoline-Class Heterocycles Hydrolysis of the Azine and Regeneration of Methyl Ethyl Ketone The hydrolysis step takes place preferably continuously, under pressure, in a reactive distillation column into which there are injected the water and the organic phase comprising the azine from steps (d) or (e).

The hydrolysis may be performed in a packed or tray distillation column, preferably operating at a pressure of 2 to 25 bar and with a bottom temperature of between 150° C. and 200° C.

While conventional packed columns may be suitable, tray columns are generally employed. Depending on the residence times allowed on the trays and the pressure, and hence the temperatures of operation, the number of trays may vary greatly. In practice, when operating under a pressure of 8 to 10 bar, the number of trays needed is of the order of 40 to 50.

Obtained following the hydrolysis are:
at the top, methyl ethyl ketone especially in the form of an azeotrope with water, and
at the bottom, an aqueous hydrazine hydrate solution.

Azine hydrolysis is known. For example, E. C. Gilbert, in an article in Journal of the American Chemical Society vol. 51, pages 3397-3409 (1929), describes equilibrium reactions of azine formation and azine hydrolysis reactions and furnishes the thermodynamic parameters of the system in the case of water-soluble azines. For example, hydrolysis of the azine of acetone is described in U.S. Pat. No. 4,724,133. For azines insoluble in aqueous solutions (for example, the azine of methyl ethyl ketone), hydrolysis must be carried out in a reactive column, such that total hydrolysis is attainable by continually isolating methyl ethyl ketone at the top of the distillation column and hydrazine hydrate at the column bottom. This system is of course at optimal operation when working continuously as described in patents FR 1 315 348 or GB 1 211 54 7, or else patent U.S. Pat. No. 4,725,421.

In all these patents reaction is carried out in a packed or, more preferably, tray distillation column operating at a pressure of 2 to 25 bar and with a bottom temperature of 150° C. to 200° C.

When working with the pure azine, i.e., that obtained for example from hydrazine hydrate and methyl ethyl ketone, it is actually found when working in accordance with these patents that dilute solutions of hydrazine hydrate are obtained with a good yield.

Taking place in this column are the hydrolysis of the azine and the isolation of hydrazine hydrate from the methyl ethyl ketone. These conditions are known. The person skilled in the art easily determines the number of trays or the height of packing, and also the water and azine feed points. Solutions with 30% or even up to 45% by weight of hydrazine hydrate are obtained at the bottom. For example, the molar water/azine ratio in the feed to this column is at least greater than the stoichiometry and advantageously between 5 and 30, preferably between 10 and 20. The temperature of the column bottom may be between 150° C. and 200° C., preferably between 175° C. and 190° C. The pressure is a function of the boiling temperature of the azine, the water and the ketone. Such hydrolysis is also described in U.S. Pat. No. 4,725,421 and in WO 00/37357.

Purge of the Pyrazoline-Class Heterocycles

According to the invention the pyrazoline-class heterocycles are purged during the hydrolysis step (f).

Depending on the number of trays or height of packing, position of the azine feed and position of the water feed, reflux, nature of the azine, etc., the person skilled in the art may easily determine that part of the column where the maximum concentration of pyrazoline-class heterocycles is obtained. It is, indeed, simpler to purge said heterocycles by withdrawal at the location of their maximum concentration, on one or more trays, for example. Withdrawal may be effected continuously or batchwise, preferably continuously.

The amount to be withdrawn is easily determinable by gas-chromatographic analysis of the concentration of these heterocycles.

Preferably the pyrazoline-class heterocycles purge is carried out by withdrawal, preferably by a continuous side takeoff.

Step (g): Recycling of the Regenerated Methyl Ethyl Ketone

The methyl ethyl ketone obtained in step (f) may be recycled to step (a).

Step (h): Recycling of the Pyrazoline-Class Heterocycles Purge

The recycling step (h) is preferably carried out continuously. The pyrazoline-class heterocycles purge obtained in step (f) may be recycled to one at least of steps (a), (b), (c), (d) or (g) of the process according to the invention, preferably to one at least of steps (c), (d) or (g). More preferably still, the pyrazoline-class heterocycles purge obtained in step (f) is recycled to the organic phase washing step (d).

Accordingly, the pyrazoline-class heterocycles purge may be recycled:
  to the aqueous phase resulting from isolation step (b), which is recycled to step (a);
  or with the methyl ethyl ketone recovered at the top of the hydrolysis column, which is recycled to step (a);
  or to the washing step (d).

BRIEF DESCRIPTION OF THE FIGURE

The FIGURE represents an example of industrial implementation of the process for preparing hydrazine hydrate according to the invention.

A shows the mekazine synthesis step (a); stream 1 comprises ammonia, hydrogen peroxide and supplementary required amounts of acetic acid, ammonium acetate or acetamide or else of methyl ethyl ketone, and also the various additives used during the synthesis step, such as the peroxide stabilizers, for example. Stream 13 corresponds to the recycling of the aqueous phase as per step (c), after it has been thermally regenerated and concentrated to remove excess water. Stream 8 corresponds to the recycling of the methyl ethyl ketone regenerated during the hydrolysis step and recovered at the exit from the hydrolysis column E as per step (g).

B shows a settler at the exit from azine synthesis step (a), which receives the reaction mixture 2. It allows the organic phase containing the crude mekazine corresponding to stream 3 and the aqueous phase containing the activator, acetamide for example, and corresponding to stream 4 to be isolated as per step (b).

C shows a countercurrent washing column as per step (d). The organic phase, stream 3, is introduced at the foot of column C and is washed in countercurrent with stream 10, corresponding to the pyrazoline-class heterocycles purge extracted from the trays of the azine hydrolysis column E as per step (h). Stream 12, corresponding to the aqueous phase at the exit from the washing column C is then sent to section G, corresponding to the step of thermal regeneration and concentration of the aqueous phase with stream 4.

The washed organic phase, stream 5, is sent for purification on a distillation column D as per step (e). With this column it is possible to recover at the top a little methyl ethyl ketone recycled at A and to remove in the bottoms the pyrazoline-class heterocycles present in the azine (not shown).

The organic phase comprising the distilled azine, stream 6, is then sent to the hydrolysis column E. The hydrolysis column E is a distillation column operating under pressure. The distilled azine, 6, is introduced into column E, as is the water, stream 7, needed for the hydrolysis.

After the hydrolysis step (f), at the top, after condensation of the vapors and decanting in F, stream 8 is obtained, comprising principally methyl ethyl ketone, water and a little azine. This phase is recycled to the azine synthesis step A.

The decanted aqueous phase, stream 9, is sent to the top of the hydrolysis column.

Stream 11 corresponds to the hydrazine hydrate solution obtained and recovered at the column bottom.

The examples are given solely for illustrative purposes and do not limit the invention.

EXAMPLES

Example 1: Preparation Process According to the Invention

The process as described for the FIGURE is employed.

Column E operates under the conditions described below:

| | |
|---|---|
| Bottom temperature | 178-190° C. |
| Overhead condenser temperature | 160° C. |
| Overhead pressure | 7.5 to 9.7 bar absolute |
| Reboiling | temperature 200° C., pressure 16 bar |
| Feed of distilled azine 6 | 5000 kg/hour |
| Feed of water 7 | 10 000 kg/hour |
| Bottom hydrazine takeoff | 12 t/h of a 22.2% aqueous solution as expressed in terms of hydrazine hydrate (or 14.2% as expressed in terms of hydrazine $N_2H_4$) |

After hydrolysis step (f), at the top, after condensation of the vapors and decanting, approximately 6 500 kg/hour of organic phase, stream 8, is withdrawn, comprising principally methyl ethyl ketone, water and a little azine. This phase is recycled to the azine synthesis step A.

The decanted aqueous phase, stream 9, is sent to the top of the hydrolysis column.

A purge, stream 10, is performed on the trays of the hydrolysis column at a rate of 1477 kg/h, at the location where the pyrazoline-class heterocycles accumulate. This purge is sent to the washing column C to wash the organic phase from the separator B.

The flow rates and analyses performed around the washing column C are reported in table 1:

TABLE 1

| | crude azine washing column C | | | | | |
|---|---|---|---|---|---|---|
| | organic phase | | | aqueous phase | | |
| | entry | exit | gain | entry | exit | gain |
| | | | stream no. | | | |
| | 3 kg/h | 5 kg/h | 5-3 kg/h | 10 kg/h | 12 kg/h | 12-10 kg/h |
| MEK | 315 | 370 | | 0.3 | 18 | |
| MEK-azine | 5416 | 5565 | 150 | 75 | 38 | −37 |
| MEK-hydrazone | 0 | 0 | | 89 | 2 | −88 |
| pyrazolines | 5 | 37 | 32 | 28 | 0 | −28 |
| acetamide | 46 | 0 | | 0 | 49 | |
| WATER | 49 | 318 | | 1137 | 777 | |
| stream total | 7006 | 7401 | | 1477 | 892 | |

It is seen that during washing of the azine stream 3 by the pyrazoline-class heterocycles purge 10, the pyrazoline-class heterocycles contained in the purge 10 are transferred virtually quantitatively into the azine stream 5 at the exit from the washing column.

It is seen that 150 kg/h of azine are thus recovered in organic phase (stream 5) when stream 3 is washed with the pyrazoline-class heterocycles purge 10. Subject to analytical uncertainties, this corresponds to the recovery of 37 and 88 kg of azine and of hydrazone contained in this purge 10.

The pyrazolines are removed during the purification of the azine by distillation of stream 5, giving the distilled azine 6, at the bottom of the distillation column with the heavy residues.

The hydrazine hydrate solution (found to contain 22.2% of hydrazine hydrate or 14.1% of hydrazine N2H4) obtained at the column bottom (stream 11) contains only a very low concentration of pyrazoline, which does not give rise to coloration problems in the final hydrazine hydrate solution obtained after concentration in the process.

An audit is also performed around the hydrolysis column E, and is reported in table 2:

| | hydrolysis columne E | | | | | |
|---|---|---|---|---|---|---|
| | washed azine | distilled washed azine | pyrazoline purge | recycled MEK | WATER | hydrazine hydrate |
| | | | | stream no. | | |
| | 5 kg/h | 6 kg/h | 10 kg/h | 8 kg/h | 7 kg/h | 11 kg/h |
| MEK | 370 | 21 | 0.3 | 5206 | | 0 |
| MEK-azine | 5565 | 5523 | 75 | 404 | | 0 |
| MEK-hpdrazone | 0 | 0 | 89 | 0 | | 6 |
| pyrazolines | 37 | 3 | 28 | 0 | 0 | 2 |
| acetamide | 0 | 0 | 0 | 0 | | 0 |
| WATER | 318 | 21 | 1137 | 849 | 11000 | 7768 |
| hydrazine N2H4 | 0 | 0 | 0 | 0 | 0 | 1305 |
| var. impurities q.s. | 792 | 136 | 0 | 330 | 0 | 104 |
| stream total | 7401 | 5987 | 1477 | 6789 | 11000 | 9186 |

The invention claimed is:

1. A process for preparing hydrazine hydrate, comprising the following steps:
   (a) reacting ammonia, hydrogen peroxide and methyl ethyl ketone in the presence of a solution comprising at least one activator to form an azine;
   (b) treating the reaction mixture from step (a) to isolate:
      an aqueous phase comprising the at least one activator; and
      an organic phase comprising the azine and optionally unreacted methyl ethyl ketone;
   (c) optionally recycling the aqueous phase to step (a) after optional treatment;
   (d) washing the organic phase;
   (e) distilling the washed organic phase to recover the azine;
   (f) hydrolyzing the azine to give hydrazine hydrate and regenerated methyl ethyl ketone, with pyrazoline-class heterocycles being purged;
   (g) optionally recycling the methyl ethyl ketone obtained in step (f) to step (a); and
   (h) recycling the pyrazoline-class heterocycles purge obtained in step (f) to one at least of steps (a), (b), (c), (d) or (g).

2. The process as claimed in claim 1, wherein the pyrazoline-class heterocycles purge obtained in step (f) is recycled to one at least of steps (c), (d) or (g).

3. The process as claimed in claim 1, wherein the pyrazoline-class heterocycles purge obtained in step (f) is recycled to the organic phase washing step (d).

4. The process as claimed in claim 3, wherein the pyrazoline-class heterocycles purge is sufficient to perform the organic phase washing, without addition of water.

5. The process as claimed in claim 1, wherein the pyrazoline-class heterocycles purge is carried out by withdrawal.

6. The process as claimed in claim 1, wherein the recycling step (h) is carried out continuously.

7. The process as claimed in claim 1, wherein the pyrazoline-class heterocycles are 3,5-diethyl-5-methylpyrazoline and 3,4,5-trimethyl-5-ethylpyrazoline.

8. The process as claimed in claim 1, wherein the azine hydrolysis and methyl ethyl ketone regeneration step (f) is performed in a packed or tray distillation column.

9. The process as claimed in claim 8, wherein the amount of pyrazoline-class heterocycles is not more than 5% by weight relative to the total weight of the liquid phase on the trays of the column or in the parts of the column at which the amount is at its maximum.

10. The process as claimed in claim 1, wherein the activator is acetamide.

* * * * *